United States Patent
Govari et al.

(10) Patent No.: US 12,336,800 B2
(45) Date of Patent: Jun. 24, 2025

(54) IMPEDANCE-BASED ABLATION INDEX FOR IRE

(71) Applicant: BIOSENSE WEBSTER (ISRAEL) LTD., Yokneam (IL)

(72) Inventors: Assaf Govari, Haifa (IL); Andres Claudio Altmann, Haifa (IL); Lilah Marziano, Ganey-Tikva (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 610 days.

(21) Appl. No.: 17/747,122

(22) Filed: May 18, 2022

(65) Prior Publication Data

US 2023/0371836 A1 Nov. 23, 2023

(51) Int. Cl.
| | | |
|---|---|---|
| A61B 18/12 | (2006.01) | |
| A61B 5/053 | (2021.01) | |
| A61B 18/14 | (2006.01) | |
| A61B 18/00 | (2006.01) | |
| A61B 34/20 | (2016.01) | |

(52) U.S. Cl.
CPC .......... *A61B 5/053* (2013.01); *A61B 18/1492* (2013.01); *A61B 2018/00577* (2013.01); *A61B 2018/00613* (2013.01); *A61B 2018/00666* (2013.01); *A61B 2018/00875* (2013.01); *A61B 2034/2046* (2016.02)

(58) Field of Classification Search
CPC . A61B 18/1206; A61B 18/1492; A61B 18/16; A61B 2018/00267; A61B 2018/00351; A61B 2018/00577; A61B 2018/00613; A61B 2018/00666; A61B 2018/00732; A61B 2018/00791; A61B 2018/00875
See application file for complete search history.

(56) References Cited

U.S. PATENT DOCUMENTS

| | | | | |
|---|---|---|---|---|
| 5,643,255 | A | * | 7/1997 | Organ ................ A61B 18/1492 606/41 |
| 6,080,149 | A | * | 6/2000 | Huang ............... A61B 18/1206 345/38 |
| 8,456,182 | B2 | | 6/2013 | Bar-Tal |
| 10,166,071 | B2 | | 1/2019 | Sherman |
| 2010/0023004 | A1 | | 1/2010 | Francischelli |

(Continued)

OTHER PUBLICATIONS

European Search Report for corresponding EPA No. 23173901.2 dated Oct. 18, 2023.

*Primary Examiner* — Daniel W Fowler

(57) ABSTRACT

A medical apparatus includes a probe, which includes an insertion tube configured for insertion into a body cavity of a patient, and a distal assembly, which is connected distally to the insertion tube and includes a plurality of electrodes, which are configured to contact tissue within the body cavity. The apparatus further includes an electrical signal generator, which is configured to apply electrical pulses to a group of two or more of the electrodes with an amplitude sufficient to irreversibly electroporate the tissue contacted by the electrodes in the group, and a controller, which is coupled to measure a change in an electrical impedance between an electrode in the group and a further electrode as a result of application of the electrical pulses and to output a measure of ablation of the tissue responsively to the measured change in the electrical impedance.

18 Claims, 3 Drawing Sheets

(56) References Cited

U.S. PATENT DOCUMENTS

| | | | |
|---|---|---|---|
| 2013/0296840 A1* | 11/2013 | Condie | A61B 90/06 |
| | | | 606/33 |
| 2018/0338793 A1* | 11/2018 | Sulkin | A61B 18/24 |
| 2019/0231421 A1* | 8/2019 | Viswanathan | A61B 18/1492 |
| 2020/0129230 A1 | 4/2020 | Forsyth | |
| 2021/0106249 A1 | 4/2021 | Schmidt | |
| 2021/0361341 A1 | 11/2021 | Neal, II | |
| 2021/0401491 A1 | 12/2021 | Altmann | |
| 2022/0022951 A1* | 1/2022 | Townley | G16H 20/30 |

* cited by examiner

IMPEDANCE-BASED ABLATION INDEX FOR IRE

FIELD OF THE DISCLOSURE

The present disclosure relates generally to medical devices, and particularly to devices and methods for irreversible electroporation of physiological tissues.

BACKGROUND

Irreversible electroporation (IRE) is a soft tissue ablation technique that applies, through a probe that is in contact with or in close proximity to the tissue, short pulses of strong electrical fields to create permanent and hence lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in all other thermal or radiation-based ablation techniques. IRE is commonly used in tumor ablation in regions where precision and conservation of the extracellular matrix, blood flow and nerves are of importance.

U.S. Pat. No. 10,166,071 describes a method of assessing a tissue ablation treatment. The method includes positioning a medical device adjacent to a target tissue, measuring a first impedance magnitude at a first frequency with the medical device, measuring a first impedance phase at a second frequency with the medical device, ablating at least a portion of the target tissue with the medical device, measuring a second impedance magnitude at a third frequency with the medical device, measuring a second impedance phase at a fourth frequency with the medical device, comparing at least one of (i) the first and second impedance magnitudes and (ii) the first and second impedance phases, and providing an indication of the efficacy of the ablation treatment based at least in part on the comparison.

United States Patent Application Publication 2021/0106249 describes a method and system for lesion formation assessment in tissue that has undergone an ablation procedure. In one example, a method of assessing lesion formation comprises: recording a baseline impedance measurement from an area of tissue with a medical device, ablating the area of tissue with the medical device, recording a post-treatment impedance measurement from the area of tissue with the medical device, identifying at least one amplitude characteristic of the baseline impedance measurement and identifying at least one amplitude characteristic of the post-treatment impedance measurement, comparing the at least one amplitude characteristic of the baseline impedance measurement and the at least one amplitude characteristic of the post-treatment impedance measurement, generating an indication of efficacy based on the comparison, the indication of efficacy being one of sufficient lesion formation and insufficient lesion formation, and re-ablating the area of tissue if the indication of efficacy is insufficient lesion formation.

United States Patent Application Publication 2021/0361341 describes a medical system for ablating a tissue site with real-time monitoring during an electroporation treatment procedure. A pulse generator generates a pre-treatment (PT) test signal prior to the treatment procedure and intra-treatment (IT) test signals during the treatment procedure. A treatment control module determines impedance values from the PT test signal and IT test signals and determines a progress of electroporation and an end point of treatment in real-time based on the determined impedance values while the treatment progresses.

SUMMARY

Examples of the present disclosure that are described hereinbelow provide improved apparatus and methods for irreversible electroporation of body tissues.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
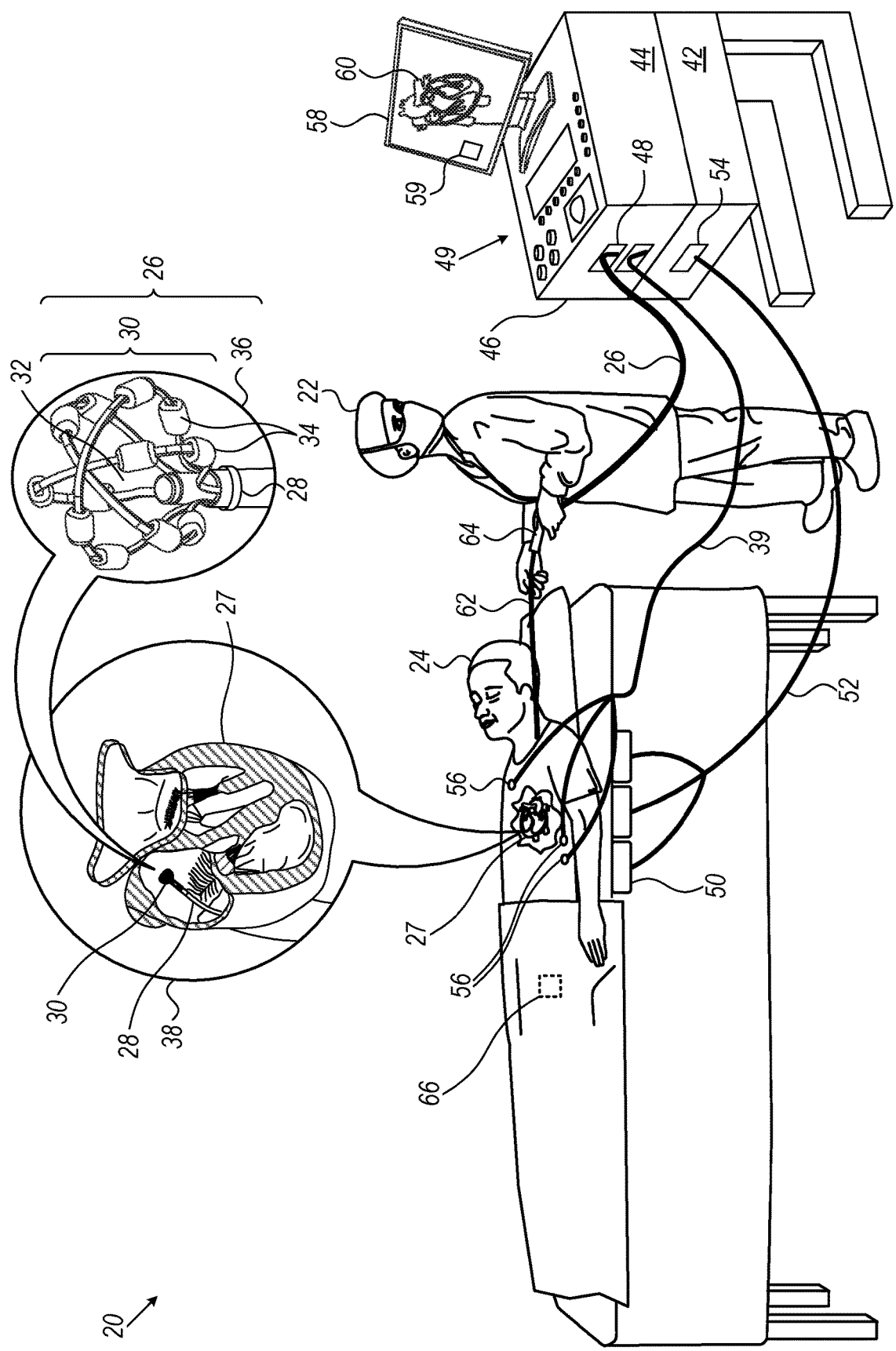
FIG. 1 is a schematic pictorial illustration of a medical apparatus in the course of an IRE procedure, in accordance with an example of the disclosure.

IRE is a predominantly non-thermal ablation process, which causes an increase of the tissue temperature by, at most, a few degrees. It thus differs from RF (radio frequency) ablation, which raises the tissue temperature by between 20 and 70° C. and destroys cells through heating. IRE utilizes biphasic pulses (combinations of positive and negative pulses) in order to avoid muscle contraction due to a nonzero DC voltage component. The pulses may be applied either in a bipolar or unipolar mode. In the bipolar mode, the electric field of the pulses is applied between two electrodes at the distal end of the catheter. In the unipolar mode, the electric field is applied between an electrode of the catheter and an external electrode on the patient's skin. The two modes are further detailed in FIG. 1 hereinbelow.

The IRE pulses are high-voltage pulses with pulse amplitudes of 500-2000 V. They are typically delivered as pulse trains with up to 100 biphasic pulses in a train, and up to 100 pulse trains in a burst of pulses. The amplitude of the pulses is typically expressed in terms of the peak pulse voltage.

It can be difficult for a physician performing an IRE procedure to be certain that an ablation lesion of sufficient depth and lateral dimensions has been formed in the patient's tissue. Application of too little energy may leave gaps between the ablation locations and be insufficient, for example, to permanently cut an arrhythmogenic current path in myocardial tissue. On the other hand, application of too much energy may cause undesirable collateral tissue damage. There is thus a need for a quantitative measure of the ablation achieved in an IRE procedure, for example in the form of a numerical ablation index. Ablation indexes that are used in the field of RF ablation depend on parameters that are not necessarily relevant to IRE and are thus unsuitable for use in IRE procedures.

The examples of the present disclosure that are described herein address this need by providing a measure of IRE ablation that is based on measurement of the electrical impedance between an IRE electrode and a further electrode, for example an external electrode on the patient's skin surface, and specifically on the change of electrical impedance over the course of an IRE ablation procedure. This measurement provides an indication of the impedance of the ablated tissue. (Alternatively or additionally, the electrical impedance may be measured between pairs of IRE electrodes.) An IRE ablation index is computed based on the change in the measured impedance. The impedance may be sensed before, during, and after the ablation. During the ablation, the impedance may be sensed during the IRE pulse trains, as well as between the trains. The IRE ablation index may reflect features such as sharp changes in the impedance, the impedance passing a predefined threshold (absolute or percentage threshold), and/or a time-integrated impedance change relative to a baseline.

In the disclosed examples, a probe, such as a catheter, comprising an insertion tube, with a distal assembly comprising multiple electrodes at its distal end, is inserted into a body cavity of a patient, such as an atrium of the patient's heart. An electrical signal generator applies electrical pulses to a group of two or more of the electrodes with amplitude sufficient to irreversibly electroporate the tissue contacted by the electrodes. A controller measures changes in the electrical impedance between an electrode in the group and a further electrode, such as an external electrode attached to the patient's skin, as a result of application of the electrical pulses and outputs a measure of ablation of the tissue based on the measured change in the electrical impedance. This measure of ablation may take the form of an ablation index, as described further hereinbelow.

System Description

FIG. 1 is a schematic pictorial illustration of a medical apparatus 20 in the course of an IRE procedure, in accordance with an example of the disclosure. A physician 22 performs the IRE procedure on a patient 24, using an electroporation catheter 26, with further details of the catheter described hereinbelow. In the pictured example, the IRE procedure is performed in a chamber of a heart 27 using a distal assembly 30 at the distal end of catheter 26. In alternative examples, the IRE procedure may be performed using other types of catheters having multiple electrodes and may be performed not only in heart 27, but also in other organs and tissue, as will be apparent to those skilled in the art after reading the present description.

As shown in an inset 36, electroporation catheter 26 comprises a shaft 28 and distal assembly 30, wherein the shaft functions as an insertion tube for inserting the distal assembly into a body cavity of patient 24, in this case into the chamber of heart 27. Distal assembly 30 comprises a basket 32 with electroporation electrodes 34 distributed along the spines of the basket. Distal assembly 30 and a part of shaft 28 are also shown in an inset 38. In alternative examples, distal assembly 30 may comprise other sorts of multi-electrode structures.

Medical apparatus 20 further comprises a controller 42 and an electrical signal generator, configured as an IRE pulse generator 44, typically residing in a console 46. The controller and the signal generator may each comprise one or several circuit components. Further details of a signal generator of this sort are described in U.S. Patent Application Publication 2021/0161592 and in U.S. patent application Ser. No. 17/092,662, filed Nov. 9, 2020, both of whose disclosures are incorporated herein by reference. Catheter 26 is connected to console 46 via an electrical interface 48, such as a port or socket, through which IRE pulses are carried from IRE pulse generator 44 to distal assembly 30. Console 40 comprises input devices 49, such as a keyboard and a mouse, as well as a display screen 58.

Controller 42 controls IRE pulse generator 44, as well as measuring the electrical impedance between a selected electrode 34 and an external electrode, also known as a "return patch" 66. Return patch 66 is coupled externally between patient 24, typically on the skin of the patient's torso, and IRE pulse generator 44. (Alternative terms for return patch 66 are "indifferent electrode" and "backpatch electrode.") Alternatively, controller 42 may measure the impedance between two selected electrodes 34.

Controller 42 typically measures the electrical impedance in a frequency range of 45-55 kHz. The inventors have observed that the electrical impedance in this range changes markedly as the result of IRE. Alternatively or additionally, other frequency ranges may be used. The inventors have found that the change in electrical impedance may be transient in nature, possibly relating to intracellular fluid that drains out of the cells during the ablation. For this reason, measurement of impedance during the IRE procedure is particularly informative.

Controller 42 receives from physician 22 (or another operator), prior to and/or during the electroporation procedure, setup parameters for the procedure. For example, using input devices 49, physician 22 defines the electrical and temporal parameters of the IRE pulses to be applied to selected electrodes 34. Physician 22 furthermore defines one or more impedance thresholds and computation methods for computing an ablation index. Controller 42 passes suitable control signals to IRE pulse generator 44 for performing the IRE.

Controller 42 may be further configured to track the respective positions of electrodes 34 during the IRE procedure, using any suitable tracking technique. For example, distal assembly 30 may comprise one or more electromagnetic position sensors (not shown), which, in the presence of an external magnetic field generated by one or more magnetic-field generators 50, output signals that vary with the positions of the sensors. Based on these signals, controller 42 may ascertain the positions of electrodes 34 within heart 27. Magnetic-field generators 50 are connected to console 46 via cables 52 and an interface 54. Alternatively or additionally, for each electrode 34, controller 42 may ascertain the respective impedances between the electrode and multiple external electrodes 56 coupled to the body surface of patient 24 at various different locations, and then compute the location of electrode 34 within heart 27 based on the ratios between these impedances. As yet another alternative, the controller may use both electromagnetic tracking and impedance-based tracking, as described, for example, in U.S. Pat. No. 8,456,182, whose disclosure is incorporated herein by reference.

Controller 42 displays on display screen 58 a window 59, showing the impedance measured over time between one or more pairs of electrodes 34, as well as an ablation index computed on the basis of the measured impedance. Optionally, window 59 may also display other ablation parameters, such as the temperature of the tissue. In some examples, controller 42 displays, on display screen 58, a relevant image 60 of the subject's anatomy, annotated, for example, to show the current position and orientation of distal assembly 30.

Controller 42 and IRE pulse generator 44 typically comprise both analog and digital elements. In an example, controller 42 comprises an analog front-end having multiple inputs with respective analog-to-digital converters (ADCs) for monitoring the IRE pulses applied by IRE pulse generator 44 to each of electrodes 34, and for monitoring the impedance between the electrodes. Controller 42 further comprises multiple digital output circuits for sending commands to IRE pulse generator 44 for adjusting the IRE pulses and for generating the display in window 59.

IRE pulse generator 44 typically comprises analog circuits for generating and amplifying the IRE pulses for electroporation, as well as digital input circuits for receiving digital control signals from controller 42.

Alternatively, the control signals may be passed from controller 42 to electric IRE pulse generator 44 in an analog form, provided that the controller and the IRE pulse generator are configured appropriately.

Typically, the functionality of controller 42, as described herein, is implemented at least partly in software. For example, controller 42 may comprise a programmed digital computing device comprising at least a central processing unit (CPU) and random-access memory (RAM). Program code, including software programs and/or data, is loaded into the RAM for execution and processing by the CPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein.

At the start of the IRE procedure, physician 22 inserts catheter 26 through a sheath 62 with basket 32 in a collapsed configuration, and only after the catheter exits the sheath is the basket extended to its intended functional shape. This functional shape is shown in inset 38. Physician 22 navigates catheter 26 to a target location in heart 27 of patient 24, by manipulating the catheter, using a manipulator 64 near the proximal end of the catheter, and/or deflection from sheath 62. Physician 22 brings distal assembly 30 into contact with tissue, such as myocardial tissue, in heart 27, for example in one of the atria of the heart. Next, under the control of physician 22 and controller 42, IRE pulse generator 44 generates IRE pulses, which are carried through catheter 26 over different respective electrical channels (not shown) to electroporation electrodes 34.

In the unipolar mode of IRE, the electroporation currents flow from one or more electroporation electrodes 34 to return patch 66.

In the bipolar mode of IRE, the electroporation currents flow between pairs or larger groups of electrodes 34 on basket 32.

Controller 42 measures the electrical impedance between pairs of electrodes 34 and computes an ablation index based on this measured impedance. Controller 42 outputs the ablation index to window 59 on display screen 58. Further details of the computation of the ablation index are described hereinbelow.

Figure 2:
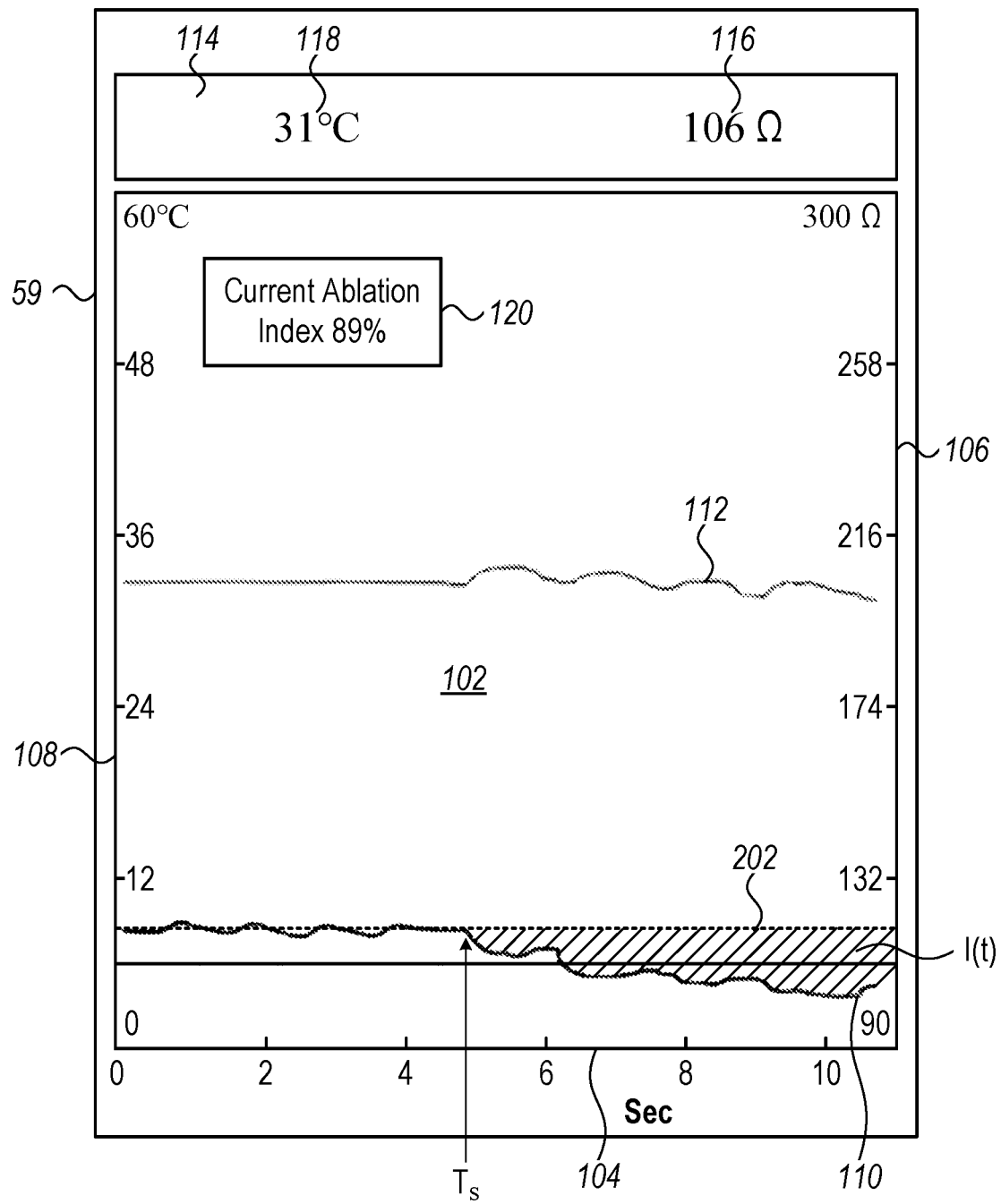
FIG. 2 is a schematic view of a display screen of a medical apparatus, illustrating a method for computing an ablation index, in accordance with an example of the disclosure.

FIG. 2 is a schematic view of window 59 on display screen 58 of apparatus 20, illustrating a method for computing an ablation index from an impedance integral, in accordance with an example of the disclosure.

Window 59 comprises a graphic display 102, with a horizontal time axis 104, a vertical impedance axis 106, and a vertical temperature axis 108. Graphic display 102 comprises a curve 110 showing the impedance measured by controller 42 as a function of measurement time, and a curve 112 showing a temperature measured by controller 42 as a function of time, for example using a temperature sensor (not shown) in distal assembly 30. A numerical display area 114 shows a current impedance 116 and a current temperature 118. An ablation index, computed by controller 42, is displayed in a text box 120. Time $T_s$ denotes the start time of the ablation. Curve 110 shows a decrease of the impedance during the ablation procedure. Curve 112 shows a steady temperature level, typical for an IRE procedure.

Controller 42 initially measures a steady-state impedance value 122, defined as the steady-state impedance before the start of the ablation, i.e., before time $T_s$. Controller 42 continually computes an integral I(t) of the difference between curve 110 and steady-state impedance value 122 up to the present time t. Controller 42 converts the integral I(t) into a suitable ablation index value, for example normalizing or otherwise scaling the present value of the integral, and displays the ablation index in a text box 120 to be viewed by physician 22. As the ablation index increases with time, physician 22 may decide at which value of the ablation index the ablation procedure should be terminated.

Figure 3:
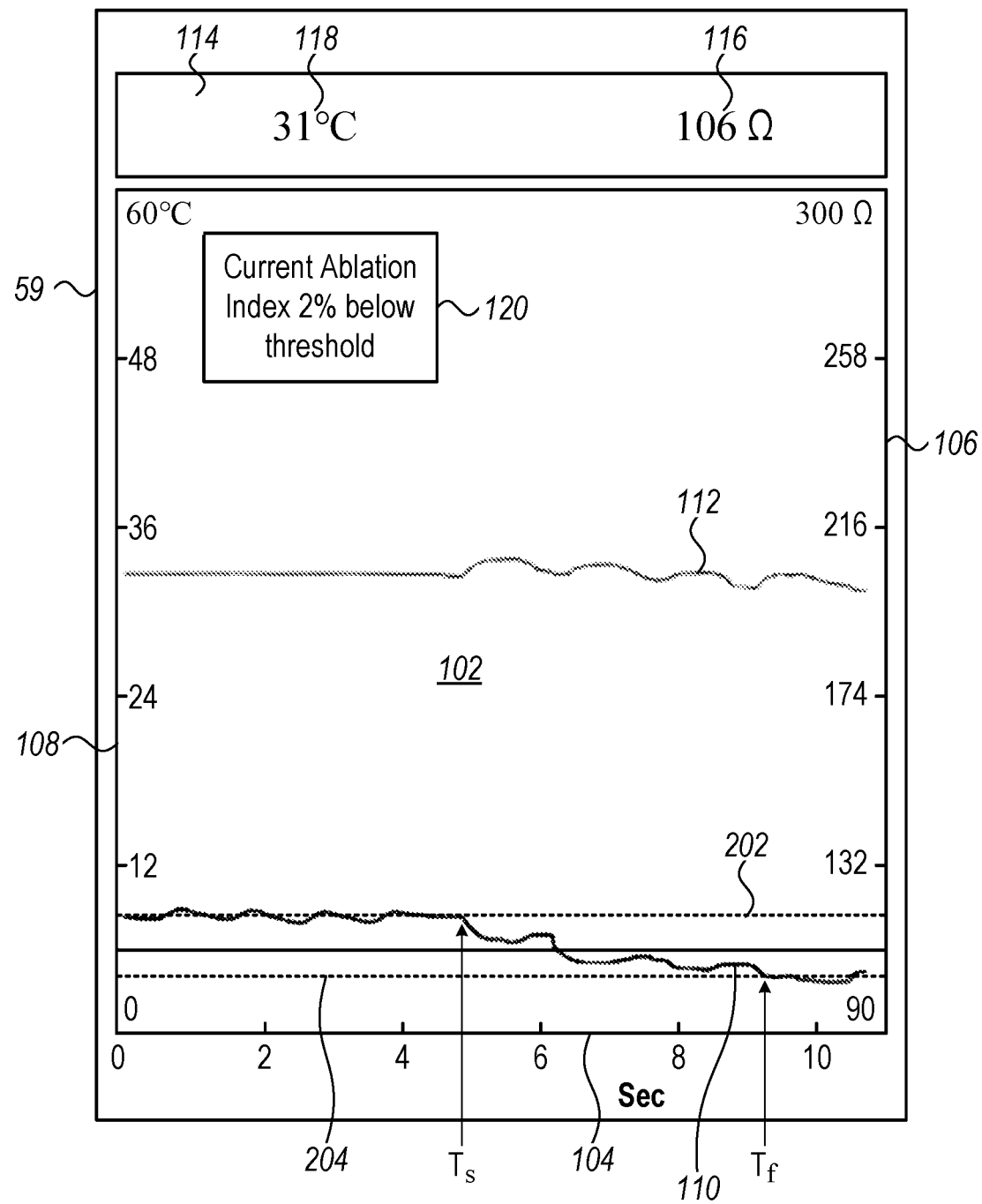
FIG. 3 is a schematic view of a display screen of a medical apparatus, illustrating a method for computing an ablation index, in accordance with another example of the disclosure.

FIG. 3 is a schematic view of window 59 of display screen 58 of apparatus 20, illustrating a method for computing an ablation index by comparing the measured impedance (as shown by curve 110) to a predefined impedance threshold 204, in accordance with an example of the disclosure. Labels from FIG. 2 are used for indicating the same or similar items in FIG. 3.

Similarly to FIG. 2, controller 42 measures a steady-state impedance value 202 before the start of the ablation. Impedance threshold 204 is defined (by physician 22 or automatically by controller 42) either as an absolute level or a level relative to steady-state impedance 202. During the ablation procedure, controller 42 monitors the impedance, shown as curve 110, and indicates to physician 22 in text box 120 whether the impedance is above or below threshold 204. Once impedance 110 falls below threshold 204 at a time $T_f$, controller 42 indicates the crossing of the threshold by a suitable message in text box 120, at which point physician 22 may choose to end the ablation procedure. The level of impedance 110 with respect to threshold 204 may be indicated either as an absolute or a relative distance from the threshold, or as a binary "above/below" message. Additionally, controller 42 may compute and display a numerical index indicating the quality of the lesion created during the ablation.

EXAMPLES

Example 1: A medical apparatus (20), comprising: a probe (26), which comprises: an insertion tube (28) configured for insertion into a body cavity of a patient (24); and a distal assembly (30), which is connected distally to the insertion tube and comprises a plurality of electrodes (34), which are configured to contact tissue within the body cavity; an electrical signal generator (44), which is configured to apply electrical pulses to a group of two or more of the electrodes with an amplitude sufficient to irreversibly electroporate the tissue contacted by the electrodes in the group; and a controller (42), which is coupled to measure a change in an electrical impedance between an electrode in the group and a further electrode as a result of application of the electrical pulses and to output a measure of ablation of the tissue responsively to the measured change in the electrical impedance.

Example 2: The apparatus according to example 1, wherein the further electrode is attached to a skin surface of the patient.

Example 3: The apparatus according to example 1, wherein the controller is configured to measure the change in the electrical impedance in a frequency range from 45 kHz to 55 kHz.

Example 4: The apparatus according to example 1, wherein the controller is configured to measure the change in the electrical impedance while the electrical signal generator is applying the electrical pulses.

Example 5: The apparatus according to example 1, wherein the controller is configured to measure the change in the electrical impedance in an interval between the electrical pulses.

Example 6: The apparatus according to example 1, wherein the measure of the ablation comprises a numerical index based on an integral of the measured change of the electrical impedance over time.

Example 7: The apparatus according to example 1, wherein the measure of the ablation comprises a numerical index based on a comparison of the electrical impedance to a predefined impedance threshold.

Example 8: The apparatus according to example 1, wherein the insertion tube and the distal assembly are configured for insertion into an atrium of a heart (27) of the patient.

Example 9: The apparatus according to example 1, wherein the electrical pulses comprise biphasic pulse trains.

Example 10: A method for medical treatment, comprising: applying electrical pulses to a group of two or more of electrodes (34) on a probe (26), which is inserted into a body cavity of a patient (24) and brought into contact with tissue in the body cavity, with an amplitude sufficient to irreversibly electroporate the tissue contacted by the electrodes in the group; measuring a change in an electrical impedance between an electrode in the group and a further electrode as a result of application of the electrical pulses; and outputting a measure of ablation of the tissue responsively to the measured change in the electrical impedance.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
a probe, which comprises:
an insertion tube configured for insertion into a body cavity of a patient; and
a distal assembly, which is connected distally to the insertion tube and comprises a plurality of electrodes, which are configured to contact tissue within the body cavity;
an electrical signal generator, which is configured to apply electrical pulses over an ablation interval to a group of two or more of the electrodes with an amplitude sufficient to irreversibly electroporate the tissue contacted by the electrodes in the group; and
a controller, which is:
coupled to measure a change in an electrical impedance between an electrode in the group and a further electrode as a result of application of the electrical pulses, and
configured to:
determine a steady-state level of impedance before the ablation interval is initiated;
compute a running integral of a difference between impedance measured over the ablation interval and the steady-state impedance, and
output to a display screen a numerical index that is a measure of ablation of the tissue responsively to the running integral computed.

2. The apparatus according to claim 1, wherein the further electrode is configured to be attached to a skin surface of the patient.

3. The apparatus according to claim 1, wherein the controller is configured to measure the change in the electrical impedance in a frequency range from 45 kHz to 55 kHz.

4. Apparatus according to claim 1, wherein the controller is configured to measure the change in the electrical impedance while the electrical signal generator is applying the electrical pulses.

5. The apparatus according to claim 1, wherein the controller is configured to measure the change in the electrical impedance in an interval between the electrical pulses.

6. The apparatus according to claim 1, wherein the controller is further configured to normalize or scale the running integral and wherein the measure of the ablation comprises a numerical index based on the normalized or scaled running integral over time.

7. The apparatus according to claim 1, wherein the measure of the ablation comprises a numerical index based on a comparison of the electrical impedance to a predefined impedance threshold.

8. The apparatus according to claim 1, wherein the insertion tube and the distal assembly are configured for insertion into an atrium of a heart of the patient.

9. The apparatus according to claim 1, wherein the electrical pulses comprise biphasic pulse trains.

10. A method for medical treatment, comprising:
applying electrical pulses over an ablation interval to a group of two or more of electrodes on a probe, which is inserted into a body cavity of a patient and brought into contact with tissue in the body cavity, with an amplitude sufficient to irreversibly electroporate the tissue contacted by the electrodes in the group;
prior to initiating the ablation interval, determining a steady-state level of impedance;
over the ablation interval, computing a running integral of a difference between impedance measured and the steady-state impedance; and
outputting on a display screen a numerical index that is a measure of ablation of the tissue responsively to the running integral computed.

11. The method according to claim 10, wherein the further electrode is attached to a skin surface of the patient.

12. The method according to claim 10, wherein measuring a change in an electrical impedance comprises measuring the change in an electrical impedance in a frequency range from 45 kHz to 55 kHz.

13. The method according to claim 10, wherein the change in the electrical impedance while the electrical signal generator is measured while applying the electrical pulses.

14. Method according to claim 10, wherein the change in the electrical impedance is measured in an interval between the electrical pulses.

15. The method according to claim 10, further comprising normalizing or scaling the running integral, wherein the measure of the ablation comprises a numerical index based on the normalized or scaled running integral over time.

16. The method according to claim 10, wherein the measure of the ablation comprises a numerical index based on a comparison of the electrical impedance to a predefined impedance threshold.

17. The method according to claim 10, wherein applying the electrical pulses comprises ablating the tissue in an atrium of a heart of the patient.

18. The method according to claim 10, wherein the electrical pulses comprise biphasic pulse trains.

* * * * *